United States Patent [19]

Bunner

[11] 4,319,482
[45] Mar. 16, 1982

[54] GAS SENSOR

[75] Inventor: Thomas A. Bunner, Abilene, Tex.

[73] Assignee: FerreTronics, Inc., Abilene, Tex.

[21] Appl. No.: 128,886

[22] Filed: Mar. 10, 1980

[51] Int. Cl.³ .......................................... E21B 47/00
[52] U.S. Cl. .................................................. 73/153
[58] Field of Search .................. 73/153, 23, 421 B; 23/230 EP; 422/68; 175/40

[56] References Cited

U.S. PATENT DOCUMENTS

| | | | |
|---|---|---|---|
| 2,112,845 | 4/1938 | Howell . | |
| 2,400,046 | 5/1946 | Hummel . | |
| 2,591,737 | 4/1952 | Souther, Jr. | 23/230 EP |
| 2,704,658 | 3/1955 | Gordon | 259/8 |
| 2,883,856 | 4/1959 | Youngman . | |
| 3,686,655 | 8/1972 | Kasahara | 340/237 R |
| 3,864,628 | 2/1975 | Klass et al. | 324/71 SN |
| 3,943,750 | 3/1976 | McLaughlin | 73/23 |
| 4,250,142 | 2/1981 | Kollmai | 73/23 X |

OTHER PUBLICATIONS

Brochure entitled "Figaro Gas Sensor TGS", #812.

*Primary Examiner*—Jerry W. Myracle
*Attorney, Agent, or Firm*—Richards, Harris & Medlock

[57] ABSTRACT

A detection unit (20) for detecting hydrocarbon gases includes a cylindrical housing (20) having a pair of opposed rectangular slots (56, 58) formed in the wall of the housing near the lower end (52). A support (60) is mounted within the housing (50) adjacent the upper end (54). A pair of baffle plates (62, 64) are mounted within the housing from the walls thereof. A semiconductor hydrocarbon gas detector (61) is mounted to the support (60) and is connected by electrical leads (30) to an analyzer and recorder (28). The detection unit (20) is mounted at the mouth of an oil or gas drilling rig and receives drilling mud into the housing (50) at the rectangular slots (56, 58) such that gases released from the drilling mud are analyzed by the gas detector (61) to determine the hydrocarbon gas content therein.

15 Claims, 4 Drawing Figures

GAS SENSOR

TECHNICAL FIELD

The present invention relates to an apparatus for detecting hydrocarbon gases released from drilling mud used in oil or gas drilling operations.

BACKGROUND ART

In oil and gas exploration, several techniques are used to determine whether deposits of oil and/or natural gas exist at a particular site. One method to determine whether drilling operations should be continued at a particular site involves the analysis of gases contained within the drilling mud used in the drilling operation.

In most drilling operations, drilling mud is circulated around the drill bit during the drilling operation. This mud is circulated to the surface of the drill site and carries with it debris and cuttings resulting from drilling. As this mud surfaces to the lower atmospheric pressure, gases which have become trapped in the mud during drilling are released.

In the past, these gases have been analyzed to determine their hydrocarbon content. Knowing the presence and concentration of hydrocarbon gases in the drilling mud provides an indication of the formation confronted by the drill bit and provides a basis for determining the feasibility of obtaining oil and gas from the well.

In prior art devices used for detecting and analyzing these gases, highly sophisticated and temperamental equipment, generally employing a Wheatstone bridge arrangement, has been required to make the analysis. As a result, this equipment has normally been housed at a location remote from the drilling site in a controlled atmosphere. As a result of this remote positioning, these systems have required means for transporting gas released from the drilling mud to the analyzing apparatus. This has normally taken the form of delivery and return hoses and a vacuum system for drawing off the gases from the mud and delivering them to the detector. Such a vacuum system has normally required a pump either electrically or engine driven.

These systems have generally been unreliable and difficult to maintain. Gas detecting units at well sites are used in all types of weather conditions and must be operable twenty-four hours a day, seven days a week. Where the prior art units are operated in severe weather climates, such as subzero temperatures, the delivery lines to the system are frequently clogged by freezing of water vapor therein. Where freezing occurs, the units must be shut down and the lines thawed before the system can be made operable. Regardless of the weather conditions, these lines are subject to being clogged by debris or other contaminants drawn into the lines with the gases. Problems have also been encountered in preventing damage to the lines due to their proximity to the rigorous work environment around the drill site. The costs of the prior art units have been substantial because of the numerous components required, as well as the difficulty encountered in continuously maintaining such equipment and its components.

Thus, a need has arisen for a hydrocarbon detector unit for use in oil and gas drilling operations which is substantially simpler, more reliable and provides a high sensitivity at a reduced cost.

DISCLOSURE OF THE INVENTION

The present invention provides an improved hydrocarbon gas detector for use with oil and gas drilling operations. The present invention provides a unit simpler than the prior units having a greater reliability providing equal sensitivity to prior art detectors. In accordance with one embodiment of the invention, an apparatus for sensing hydrocarbon gases released from drilling mud used in oil and gas drilling operations includes a housing having an opening located in the lower portion of the housing for receiving the drilling mud therein. The housing is supported by a first support structure such that the opening is positioned to receive the mud from the drilling operation. A second support structure is positioned in the housing near the upper end thereof and above the opening. A hydrocarbon sensor is mounted on the second support structure for detecting hydrocarbon gases released from the drilling mud as they pass through the housing. In accordance with a more specific feature of the invention, the hydrocarbon sensor is a semiconductor detector.

In accordance with a more specific embodiment of the invention, the opening in the housing includes a pair of openings on opposite sides of the housing. The housing is aligned with respect to the flow of mud from the drill site such that the mud flows into the housing through one of the openings and exits through the other opening. In one embodiment of the invention, the housing also includes baffles mounted between the openings in the housing and the second support structure be prevent deposit of mud and other contaminants on the sensor. The baffles shield the sensor from the mud passing therebelow while permitting gases to move freely from the drilling mud to contact with the sensor.

In accordance with still a further embodiment of the invention, the housing consists of a cylindrical tube having an upper and lower end with the openings in the side wall of the tube adjacent the lower end. The second support structure is mounted from the walls of the tubing adjacent the upper end thereof. A removable hood is received on the upper end of the housing with the sensor positioned therebelow. In this embodiment, the sensor is accessible by removal of the hood.

In operation of the present invention, the housing is placed at or very near the mouth of the drill site such that drilling mud delivered from the well is directed through the housing. Because the detector is mounted directly in the housing, the need for a remote facility for housing the detector, suction lines and apparatus for drawing a suction to deliver gases from the drilling mud to a remote site, are all eliminated. With the elimination of the suction apparatus as well as the conduits required to deliver the gases to a remote site, the problems associated with these elements are also eliminated. Thus, problems of line freezing and malfunction of the vacuum devices are no longer potential problems in the present invention.

The present invention further employs a gas sensor semiconductor detector of the type produced by Figaro Engineering, Inc. and identified as the TGS gas sensors. These sensors are highly sensitive and substantially less temperamental than the prior art units normally employing a Wheatstone bridge arrangement. These detectors in coordination with a recorder provide an instantaneous indication of the presence of hydrocarbon gases. Further, the present sensor may be operated on a 12 volt DC battery with very low amperage. The present system also is substantially less complex and therefore less costly to produce.

By using a gas sensor semiconductor detector, recording of hydrocarbon gases occurs simultaneously with sensing of the gas. Thus, the present system eliminates any lag time between sensing and recording of hydrocarbon gases.

BRIEF DESCRIPTION OF THE DRAWINGS

For a more complete understanding of the present invention, and for further details and advantages thereof, reference is now made to the following Detailed Description taken in conjunction with the accompanying Drawings, in which.

DESCRIPTION OF THE PREFERRED EMBODIMENTS

In oil and gas drilling operations, drilling mud is continuously circulated into and out of the well to the drill bit to facilitate the drilling operation. When the drill bit reaches formation containing hydrocarbon gases, these gases go in a solution with the mud and surface with it. Upon surfacing to the lower atmospheric pressure, the gases are released from the mud. The present invention provides a detector for sensing and recording the hydrocarbon gases released from drilling mud. Through detection of the hydrocarbon gases, the presence of oil or gas can be determined.

Figure 1:
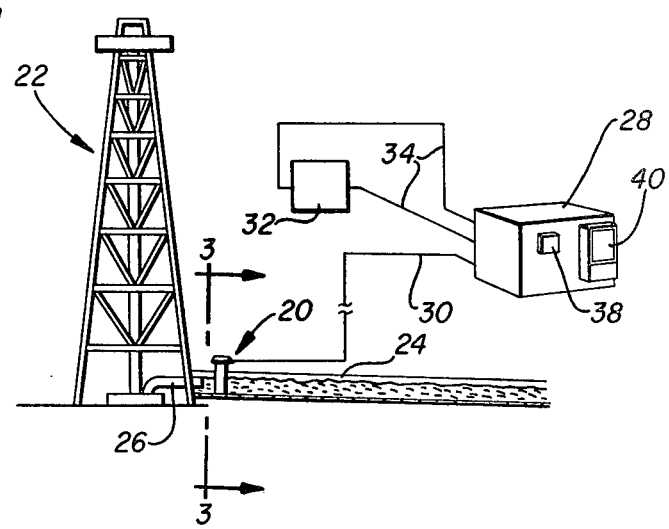
FIG. 1 is a schematic representation of the present invention in its primary embodiment.

FIG. 1 illustrates a detection unit 20 according to the present invention for detecting hydrocarbon gases released from the drilling mud. Unit 20 is positioned at the mouth of drilling unit 22. The unit is positioned in a mud ditch 24 fed by a discharge conduit 26. As will be appreciated by those skilled in the art, it will be understood that unit 20 may be positioned either in a mud ditch designed to carry the circulating mud away from the drill site or in a mud tank where the drilling mud is collected prior to disposal or recirculation. Unit 20 is connected to an analyzer and recorder 28 by appropriate electrical leads 30. Analyzer and recorder 28 is powered by a power source 32 and connected thereto by appropriate electrical leads 34. Analyzer and recorder 28 includes a supply voltage indicator 38 and a recorder 40. Analyzer and recorder 28 may be one of several commercially available units, such as the unit marketed under the trade name "Rustrak" by Gulton Industries, of Manchester, New Hampshire.

Figure 3:
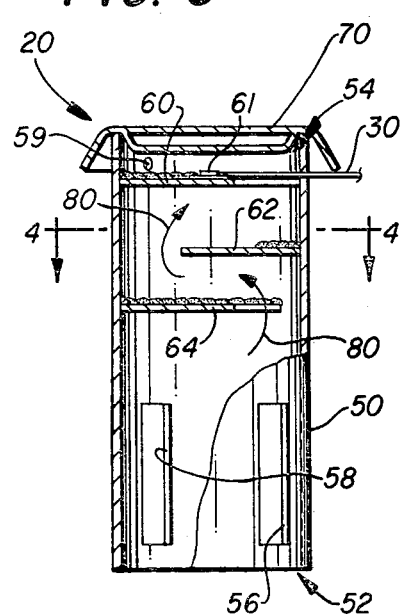
FIG. 3 illustrates a vertical section view taken along line 3—3 of FIG. 1 showing the sensing unit of the present invention partially broken away to reveal the interior thereof.
Figure 2:
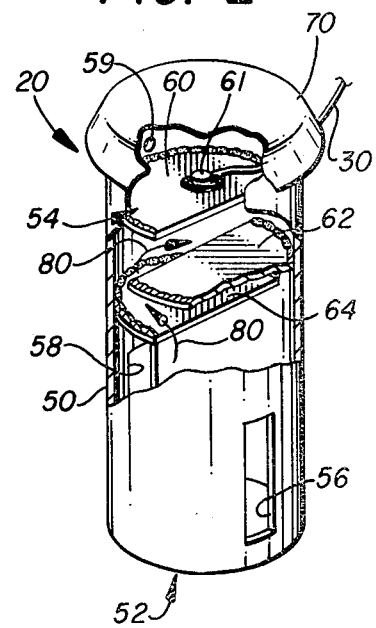
FIG. 2 is a perspective, partially broken away view of the detector of the present invention.
Figure 4:
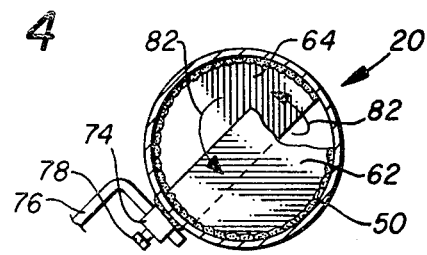
FIG. 4 illustrates a horizontal section view taken along line 4—4 of FIG. 3.

Referring now to FIGS. 2 and 3, wherein a perspective partially broken away view and a vertical section view, respectively, are illustrated, unit 20 includes a cylindrical housing 50 having an opening at the lower end 52 and at the upper end 54. A pair of opposed rectangular slots 56 and 58 are formed in the side wall of housing 50 near lower end 52. A plurality of ports 59 are formed in the walls of housing 50 near the upper end 65 thereon. A support shelf 60 is mounted within housing 50 adjacent to upper end 54. Shelf 60 extends substantially over half of the cross section of housing 50 and is appropriately attached thereto. A hydrocarbon sensor 61 is mounted to shelf 60 and electrical leads 30 are connected therefrom for connection of the sensor to analyzer and recorder 28 (FIG. 1). As shown in FIG. 2, shelf 60 is positioned below ports 59. A pair of baffle plates 62 and 64 are mounted within housing 50 from the walls thereof, being attached thereto by appropriate means such as welding or the like. As can be seen in FIG. 4, baffles 62 and 64 extend slightly over more than half of the cross sectional area of housing 50 and overlap to provide a complete shield between the lower end of housing 50 and sensor 61. As shown in FIG. 2, baffle plate 64 extends from the wall of housing 50 opposite slot 56. Thus, baffle plate 64 is positioned to most effectively prevent upward sloshing of mud entering housing 50 through slot 56.

A removable dome 70 is received on and closes the upper end 54 of housing 50. A support bracket 74 is mounted to the exterior of housing 50, and arm 76 is received within bracket 74 and is retained therein by set bolts 78.

In operation of the unit, sensing unit 20 is positioned in drilling mud ditch 24 such that the top of slots 56 and 58 are slightly above level of the mud being carried from the well. An air gap is provided by positioning the tops of slots 56 and 58 slightly above the level of mud carried from the well. This air gap may be varied in size by varying the position of the top of slots 56 and 58 relative to the level of mud flowing therethrough to control and facilitate a draft into housing 50 and upwardly toward sensor 61. Air continues in a circulatory path past sensor 61 and out of ports 59 adjacent to sensor 61. In a primary embodiment of the invention, the unit is oriented such that slots 56 and 58 are in line with the flow of mud in ditch 24. Arm 76 is supported from a support frame (not shown) adjacent to ditch 24. This frame is vertically adjustable such that arm 76 and thus sensing unit 20, may be positioned to tops of the slots 56 and 58 slightly above the surface of the mud flowing in ditch 24.

As drilling mud passes into slot 56 and within housing 50, a turbulence is created and gases are released from the mud, communicate past baffles 62 and 64 and contact sensor 61. Flow of such gases follow the general movement indicated by arrows 80 (FIG. 4). Thus, although the gases from the mud passing into housing 50 may contact sensor 61, baffles 62 and 64 act as a shield to prevent the sloshing of mud and contaminants onto sensor 61. By passing an appropriate current through sensor 61 and measuring the conductivity thereof, an accurate indication of the hydrocarbon content of the gases within housing 50 may be determined by analyzer and recorder 28 and this information plotted for use in determining the presence of hydrocarbon gases at the drilling depth associated therewith. The mud passes through and out of housing 50 by way of slot 58. It will, of course, be understood by those skilled in the art that in addition to providing a signal to analyzer and recorder 28, sensor 61 may operate on alarm devices, such as a light or buzzer, when a specific level of hydrocarbon gas concentration is detected by the sensor.

Dome 70 is readily removable from housing 50 to permit access to and repair and replacement, as required, of sensor 61 and leads 30. While the embodiment illustrated shows sensor 61 attached to shelf 60, it will be understood that the sensor may be mounted at alternative locations in the upper part of unit 20. For example, sensor 61 may be mounted to an interiorly facing surface of dome 70 or to the wall of housing 50.

Hydrocarbon gas detector 61 is a semiconductor detector of the type manufactured and sold by Figaro Engineering, Inc., Toyonaka City, Osaka, Japan. These semiconductor detectors, identified under the designation TGS gas sensitive semiconductor sensors, are based on N type sintered tin dioxide ($SnO_2$). These detectors operate to indicate the presence of hydrocarbon gases as a result of their marked decrease in electrical resistance in the presence of hydrocarbon gases. Because the sensor of the type used in the present invention may be incorporated directly in sensor unit 20 at the mouth of the drill site, several advantages are achieved. By using a sensor which is less temperamental than the prior art units involving the Wheatstone bridge arrangements, there is no need to position the sensor remote from the mouth of the drill site. Thus, there is no need to draw off the gases from the drilling mud or transport them to a remote location. The apparatus required in the prior art systems for accomplishing the transportation of the gas to a remote location is then eliminated. As a result, the present system is substantially simplified over prior art units and reliability is improved. The problems heretofore encountered in severe weather conditions and the attendant freezing of the lines carrying the gases to be analyzed to a remote location are eliminated. Likewise, the possibility of such lines being plugged by foreign matter is also no longer a concern because of the arrangement of the present invention.

The present invention also 20 incorporates an analyzer and recorder which operates on a twelve volt DC power source. Because of the very low amperage required to operate the unit, providing continuous power to the unit is greatly simplified.

The present invention also provides a sensing unit which is as sensitive as prior art units as a result of the use of the semiconductor detectors of the type described above. Further, because the sensing unit may be placed at the mouth of the drilling well, a reading of the hydrocarbon content in the drilling mud substantially corresponds with the drill depth at the time of the reading. Exact correlation between the drilling depth and the hydrocarbon gases encountered thereat can be more accurately calculated to identify favorable drilling depths. Further, the present invention, because of its simplicity, may be produced at a cost substantially below that of the prior art units.

Although preferred embodiments of the invention have been described in the foregoing Detailed Description and illustrated in the accompanying Drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications and substitutions of parts and elements as fall within the spirit and scope of the invention.

I claim:

1. In an oil or gas drilling operation, an apparatus for sensing hydrocarbon gases released from drilling mud used in the drilling operation, comprising:
   a housing having an opening in the lower portion thereof for receiving the drilling mud therein,
   first means for supporting said housing with said opening positioned to receive mud from the drilling operation therein and with an upper portion of the housing above the normal level of the drilling mud,
   second means positioned in the upper portion above the openings in said housing for receiving a hydrocarbon sensor thereon, and
   a hydrocarbon semiconductor detector sensor mounted on said second means for detecting hydrocarbon gases released from the drilling mud.

2. The apparatus according to claim 1 wherein the opening in said housing includes a pair of apertures on opposite sides of said housing, one of said openings permitting the entry of said mud into said housing and the other of said openings permitting the flow of said mud out of said housing.

3. The apparatus according to claim 1 wherein said opening in said housing is positioned with its upper portion above the lever of mud received in said housing to permit air into said housing through said opening and further comprising a port in the housing adjacent the upper end to permit an upward draft of air through the housing.

4. The apparatus according to claim 1 further comprising baffle means mounted between the opening in said housing and said second means to prevent deposit of mud on said sensor.

5. The apparatus according to claim 1 further comprising a removable hood on the upper end of said housing, said sensor being positioned below said hood and accessible by removal of said hood.

6. The apparatus according to claim 1 wherein said housing is a cylindrical tube having upper and lower ends with said opening in the wall of said tubing adjacent said lower end and said second means supported from the side walls of the tube adjacent the upper end thereof.

7. An apparatus for sensing hydrocarbon gases released from a drilling fluid circulated to facilitate the drilling of an oil or gas well, comprising:
   a housing having upper and lower ends with an opening in the lower end thereof,
   support means for supporting said housing with the opening in said lower end in communication with the drilling fluid such that hydrocarbon gases released from the fluid are received within said housing,
   a support positioned in said housing and above said opening in the lower end, said support being positioned adjacent said upper end, and
   a hydrocarbon semiconductor detector sensor mounted on said support means for detecting hydrocarbon gases released from the drilling fluid.

8. The apparatus according to claim 7 wherein said opening in said housing is positioned with its upper portion above the level of mud received in said housing to permit air into said housing through said opening and further comprising a port in the housing adjacent the upper end to permit an upward draft of air through the housing.

9. The apparatus according to claim 7 wherein the opening in said housing includes a pair of apertures on opposite sides of said housing, one of said openings permitting the entry of said fluid into said housing and the other of said openings permitting the flow of said fluid out of said housing.

10. The apparatus according to claim 7 further comprising baffle means mounted between the opening in said housing and said support to prevent deposit of fluid on said sensor.

11. The apparatus according to claim 7 further comprising a removable hood on the upper end of said housing, said sensor being positioned below said hood and accessible by removal of said hood.

12. The apparatus according to claim 7 wherein said housing is a cylindrical tube having upper and lower ends with said opening in the wall of said tubing adjacent said lower end and said support supported from the wall of the tubing adjacent the upper end thereof.

13. In an oil or gas drilling operation, a method for detecting hydrocarbon gases released from drilling mud used in the drilling operation, comprising:

receiving the drilling mud from the mouth of the well through a housing, positioning a hydrocarbon semiconductor detector in the housing above the flow of mud therethrough to produce a signal in response to the presence of hydrocarbon gas, and transmitting the signal from the detector to a remote recorder.

14. The method according to claim 13 further comprising:

positioning baffles between the flow of mud in the housing and the detector to prevent the deposit of mud on the detector.

15. The method according to claim 13 further comprising:

providing a movement of air from adjacent the flow of mud through the housing to the detector.

* * * * *